(12) United States Patent
Houser et al.

(10) Patent No.: US 10,973,563 B2
(45) Date of Patent: Apr. 13, 2021

(54) SURGICAL INSTRUMENT WITH CHARGING DEVICES

(71) Applicant: ETHICON LLC, Guaynabo, PR (US)

(72) Inventors: Kevin L. Houser, Springboro, OH (US); David C. Yates, West Chester, OH (US); John W. Willis, Milford, OH (US); Aron O. Zingman, Cambridge, MA (US); Donna L. Korvick, San Antonio, TX (US); Ashvani K. Madan, Mason, OH (US)

(73) Assignee: Ethicon LLC, Guaynabo, PR (US)

( * ) Notice: Subject to any disclaimer, the term of this patent is extended or adjusted under 35 U.S.C. 154(b) by 982 days.

(21) Appl. No.: 15/460,822

(22) Filed: Mar. 16, 2017

(65) Prior Publication Data

US 2017/0245913 A1 Aug. 31, 2017

Related U.S. Application Data

(62) Division of application No. 13/275,495, filed on Oct. 18, 2011, now abandoned.
(Continued)

(51) Int. Cl.
*A61B 18/12* (2006.01)
*A61B 17/285* (2006.01)
(Continued)

(52) U.S. Cl.
CPC .... *A61B 18/1206* (2013.01); *A61B 17/00234* (2013.01); *A61B 17/285* (2013.01);
(Continued)

(58) Field of Classification Search
CPC . A61B 18/1206; A61B 18/1445; A61B 34/30; H02J 2007/0067; H02J 7/0063
(Continued)

(56) References Cited

U.S. PATENT DOCUMENTS

| 1,754,806 A | 4/1930 | Stevenson |
| 3,297,192 A | 1/1967 | Swett |

(Continued)

FOREIGN PATENT DOCUMENTS

| DE | 102008051866 | 10/2010 |
| DE | 102009013034 | 10/2010 |

(Continued)

OTHER PUBLICATIONS

Indian Office Action, Examination Report, dated Mar. 28, 2018 for Application No. 4008/DELNP/2013, 6 pgs.
(Continued)

*Primary Examiner* — Thomas A Giuliani
*Assistant Examiner* — Christine A Dedoulis
(74) *Attorney, Agent, or Firm* — Frost Brown Todd LLC

(57) ABSTRACT

A surgical instrument includes a first power source and a second power source. The first power source is configured to deliver power to a surgical instrument at a first rate of discharge. The second power source is configured to deliver power to the first power source at a second rate of discharge. The first power source and the second power source are positioned within the surgical instrument. The first power source and the second power source are further configured to communicate with a control module. The control module may rely on power from the first power source to drive an end effector of the surgical instrument. The end effector may comprise a harmonic/ultrasonic blade, RF electrosurgical electrodes, powered cutting/stapling features, and/or various other types of components.

20 Claims, 4 Drawing Sheets

Related U.S. Application Data

(60) Provisional application No. 61/487,846, filed on May 19, 2011, provisional application No. 61/410,603, filed on Nov. 5, 2010.

(51) Int. Cl.
*A61B 18/14* (2006.01)
*A61B 17/00* (2006.01)
*H02J 7/00* (2006.01)
*A61B 34/30* (2016.01)
*A61B 90/00* (2016.01)
*A61B 17/32* (2006.01)
*A61B 17/29* (2006.01)
*A61B 18/00* (2006.01)
*G02B 27/01* (2006.01)

(52) U.S. Cl.
CPC .......... *A61B 18/1445* (2013.01); *A61B 34/30* (2016.02); *A61B 90/08* (2016.02); *H02J 7/0063* (2013.01); *A61B 2017/0046* (2013.01); *A61B 2017/00115* (2013.01); *A61B 2017/00398* (2013.01); *A61B 2017/00473* (2013.01); *A61B 2017/00477* (2013.01); *A61B 2017/00482* (2013.01); *A61B 2017/00734* (2013.01); *A61B 2017/291* (2013.01); *A61B 2017/293* (2013.01); *A61B 2017/294* (2013.01); *A61B 2017/2929* (2013.01); *A61B 2017/2931* (2013.01); *A61B 2017/2933* (2013.01); *A61B 2017/320069* (2017.08); *A61B 2017/320089* (2017.08); *A61B 2017/320094* (2017.08); *A61B 2017/320095* (2017.08); *A61B 2018/00178* (2013.01); *A61B 2018/00791* (2013.01); *A61B 2018/00988* (2013.01); *A61B 2018/1226* (2013.01); *A61B 2018/1412* (2013.01); *A61B 2018/1455* (2013.01); *A61B 2090/0803* (2016.02); *A61B 2090/0813* (2016.02); *A61B 2090/0814* (2016.02); *G02B 2027/011* (2013.01); *G02B 2027/0178* (2013.01); *H02J 2007/0067* (2013.01)

(58) Field of Classification Search
USPC .......................................................... 606/28
See application file for complete search history.

(56) References Cited

U.S. PATENT DOCUMENTS

| | | |
|---|---|---|
| 3,419,198 A | 12/1968 | Pettersen |
| 3,619,671 A | 11/1971 | Shoh |
| 4,034,762 A | 7/1977 | Cosens et al. |
| 4,057,220 A | 11/1977 | Kudlacek |
| 4,535,773 A | 8/1985 | Yoon |
| 4,641,076 A | 2/1987 | Linden et al. |
| 4,641,077 A | 2/1987 | Pascaloff |
| 4,662,068 A | 5/1987 | Polonsky |
| 4,666,037 A | 5/1987 | Weissman |
| 4,685,459 A | 8/1987 | Koch et al. |
| 4,717,018 A | 1/1988 | Sacherer et al. |
| 4,717,050 A | 1/1988 | Wright |
| 4,721,097 A | 1/1988 | D'Amelio |
| 4,768,969 A | 9/1988 | Bauer et al. |
| 4,800,878 A | 1/1989 | Cartmell |
| 4,844,259 A | 7/1989 | Glowczewskie, Jr. |
| 4,878,493 A | 11/1989 | Pasternak et al. |
| 5,071,417 A | 12/1991 | Sinofsky |
| 5,107,155 A | 4/1992 | Yamaguchi |
| 5,144,771 A | 9/1992 | Miwa |
| 5,169,733 A | 12/1992 | Savovic et al. |
| 5,176,677 A | 1/1993 | Wuchinich |
| 5,246,109 A | 9/1993 | Markle et al. |
| 5,273,177 A | 12/1993 | Campbell |
| 5,277,694 A | 1/1994 | Leysieffer et al. |
| 5,308,358 A | 5/1994 | Bond et al. |
| 5,322,055 A | 6/1994 | Davison |
| 5,339,799 A | 8/1994 | Kami et al. |
| 5,358,508 A | 10/1994 | Cobb et al. |
| 5,361,902 A | 11/1994 | Abidin et al. |
| 5,429,229 A | 7/1995 | Chester et al. |
| 5,449,370 A | 9/1995 | Vaitekunas |
| 5,454,378 A | 10/1995 | Palmer et al. |
| 5,501,607 A | 3/1996 | Yoshioka et al. |
| 5,507,297 A | 4/1996 | Slater et al. |
| 5,561,881 A | 10/1996 | Klinger et al. |
| 5,578,052 A | 11/1996 | Koros et al. |
| 5,580,258 A | 12/1996 | Wakata |
| 5,582,617 A | 12/1996 | Klieman et al. |
| 5,590,778 A | 1/1997 | Dutchik |
| 5,592,065 A | 1/1997 | Oglesbee et al. |
| 5,597,371 A | 1/1997 | Toukura |
| 5,599,350 A | 2/1997 | Schulze et al. |
| 5,630,420 A | 5/1997 | Vaitekunas |
| 5,630,456 A | 5/1997 | Hugo et al. |
| 5,690,222 A | 11/1997 | Peters |
| 5,707,369 A | 1/1998 | Vaitekunas et al. |
| 5,741,305 A | 4/1998 | Vincent et al. |
| 5,776,155 A | 7/1998 | Beaupre et al. |
| 5,800,336 A | 9/1998 | Ball et al. |
| 5,817,128 A | 10/1998 | Storz |
| 5,868,244 A | 2/1999 | Ivanov et al. |
| 5,873,873 A | 2/1999 | Smith et al. |
| 5,882,310 A | 3/1999 | Marian, Jr. |
| 5,935,144 A | 8/1999 | Estabrook |
| 5,938,633 A | 8/1999 | Beaupre |
| 5,944,737 A | 8/1999 | Tsonton et al. |
| 5,951,575 A | 9/1999 | Bolduc et al. |
| 5,980,510 A | 11/1999 | Tsonton et al. |
| 5,997,531 A | 12/1999 | Loeb et al. |
| 6,018,227 A | 1/2000 | Kumar et al. |
| 6,051,010 A | 4/2000 | Dimatteo et al. |
| 6,056,735 A | 5/2000 | Okada et al. |
| 6,063,098 A | 5/2000 | Houser et al. |
| 6,066,151 A | 5/2000 | Miyawaki et al. |
| 6,083,191 A | 7/2000 | Rose |
| 6,083,223 A | 7/2000 | Baker |
| 6,099,537 A | 8/2000 | Sugai et al. |
| 6,113,593 A | 9/2000 | Tu et al. |
| 6,123,702 A | 9/2000 | Swanson et al. |
| 6,165,191 A | 12/2000 | Shibata et al. |
| 6,190,386 B1 | 2/2001 | Rydell |
| 6,204,592 B1 | 3/2001 | Hur |
| 6,214,023 B1 | 4/2001 | Whipple et al. |
| 6,246,896 B1 | 6/2001 | Dumoulin et al. |
| 6,248,238 B1 | 6/2001 | Burtin et al. |
| 6,287,304 B1 | 9/2001 | Eggers et al. |
| 6,325,811 B1 | 12/2001 | Messerly |
| 6,339,368 B1 | 1/2002 | Leith |
| 6,398,755 B1 | 6/2002 | Belef et al. |
| 6,409,742 B1 | 6/2002 | Fulton, III et al. |
| 6,500,176 B1 | 12/2002 | Truckai et al. |
| 6,500,188 B2 | 12/2002 | Harper et al. |
| 6,512,667 B2 | 1/2003 | Shiue et al. |
| 6,514,267 B2 | 2/2003 | Jewett |
| 6,520,185 B1 | 2/2003 | Bommannan et al. |
| 6,561,983 B2 | 5/2003 | Cronin et al. |
| 6,562,032 B1 | 5/2003 | Ellman et al. |
| 6,609,414 B2 | 8/2003 | Mayer et al. |
| 6,622,731 B2 | 9/2003 | Daniel et al. |
| 6,623,500 B1 | 9/2003 | Cook et al. |
| 6,626,901 B1 | 9/2003 | Treat et al. |
| 6,647,281 B2 | 11/2003 | Morency |
| 6,650,091 B1 | 11/2003 | Shiue et al. |
| 6,650,975 B2 | 11/2003 | Ruffner |
| 6,656,177 B2 | 12/2003 | Truckai et al. |
| 6,658,301 B2 | 12/2003 | Loeb et al. |
| 6,666,875 B1 | 12/2003 | Sakurai et al. |
| 6,706,038 B2 | 3/2004 | Francischelli et al. |
| 6,717,193 B2 | 4/2004 | Olewine et al. |
| 6,730,042 B2 | 5/2004 | Fulton et al. |

(56) References Cited

U.S. PATENT DOCUMENTS

| | | |
|---|---|---|
| 6,753,673 B2 | 6/2004 | Shiue et al. |
| 6,758,855 B2 | 7/2004 | Fulton, III et al. |
| 6,761,698 B2 | 7/2004 | Shibata et al. |
| 6,761,701 B2 | 7/2004 | Cucin |
| 6,783,524 B2 | 8/2004 | Anderson et al. |
| 6,815,206 B2 | 11/2004 | Lin et al. |
| 6,821,671 B2 | 11/2004 | Hinton et al. |
| 6,836,097 B2 | 12/2004 | Turner et al. |
| 6,838,862 B2 | 1/2005 | Luu |
| 6,847,192 B2 | 1/2005 | Turner et al. |
| 6,860,880 B2 | 3/2005 | Treat et al. |
| 6,869,435 B2 | 3/2005 | Blake |
| 6,923,807 B2 | 8/2005 | Ryan et al. |
| 6,982,696 B1 | 1/2006 | Shahoian |
| 6,998,822 B2 | 2/2006 | Turner et al. |
| 7,031,155 B2 | 4/2006 | Sauciuc et al. |
| 7,061,749 B2 | 6/2006 | Liu et al. |
| 7,077,853 B2 | 7/2006 | Kramer et al. |
| 7,083,589 B2 | 8/2006 | Banko et al. |
| 7,085,123 B2 | 8/2006 | Shiue et al. |
| 7,101,371 B2 | 9/2006 | Dycus et al. |
| 7,112,201 B2 | 9/2006 | Truckai et al. |
| 7,125,409 B2 | 10/2006 | Truckai et al. |
| 7,150,712 B2 | 12/2006 | Buehlmann et al. |
| 7,160,132 B2 | 1/2007 | Phillips et al. |
| 7,169,146 B2 | 1/2007 | Truckai et al. |
| 7,186,253 B2 | 3/2007 | Truckai et al. |
| 7,186,473 B2 | 3/2007 | Shiue et al. |
| 7,189,233 B2 | 3/2007 | Truckai et al. |
| 7,220,951 B2 | 5/2007 | Truckai et al. |
| 7,221,216 B2 | 5/2007 | Nguyen |
| 7,232,440 B2 | 6/2007 | Dumbauld et al. |
| 7,244,024 B2 | 7/2007 | Biscardi |
| 7,292,227 B2 | 11/2007 | Fukumoto et al. |
| 7,296,804 B2 | 11/2007 | Lechot et al. |
| 7,303,556 B2 | 12/2007 | Metzger |
| 7,309,849 B2 | 12/2007 | Truckai et al. |
| 7,311,709 B2 | 12/2007 | Truckai et al. |
| 7,349,741 B2 | 3/2008 | Maltan et al. |
| 7,353,068 B2 | 4/2008 | Tanaka et al. |
| 7,354,440 B2 | 4/2008 | Truckai et al. |
| 7,364,061 B2 | 4/2008 | Swayze et al. |
| 7,364,554 B2 | 4/2008 | Bolze et al. |
| 7,375,644 B2 | 5/2008 | Miyazawa |
| 7,381,209 B2 | 6/2008 | Truckai et al. |
| 7,416,101 B2 | 8/2008 | Shelton, IV et al. |
| 7,422,139 B2 | 9/2008 | Shelton, IV et al. |
| 7,464,846 B2 | 12/2008 | Shelton, IV et al. |
| 7,470,237 B2 | 12/2008 | Beckman et al. |
| 7,473,145 B2 | 1/2009 | Ehr et al. |
| 7,479,152 B2 | 1/2009 | Fulton, III et al. |
| 7,494,492 B2 | 2/2009 | Da Silva et al. |
| D594,983 S | 6/2009 | Price et al. |
| 7,560,903 B2 | 7/2009 | Thrap |
| 7,563,142 B1 | 7/2009 | Wenger et al. |
| 7,570,994 B2 | 8/2009 | Tamura et al. |
| 7,573,151 B2 | 8/2009 | Acena et al. |
| 7,583,564 B2 | 9/2009 | Kitahara et al. |
| 7,638,958 B2 | 12/2009 | Philipp et al. |
| 7,643,378 B2 | 1/2010 | Genosar |
| 7,658,247 B2 | 2/2010 | Carter |
| 7,692,411 B2 | 4/2010 | Trainor et al. |
| 7,699,850 B2 | 4/2010 | Miller |
| 7,699,856 B2 | 4/2010 | Van Wyk et al. |
| 7,717,312 B2 | 5/2010 | Beetel |
| 7,721,936 B2 | 5/2010 | Shalton, IV et al. |
| 7,738,971 B2 | 6/2010 | Swayze et al. |
| 7,761,198 B2 | 7/2010 | Bhardwaj |
| 7,766,910 B2 | 8/2010 | Hixson et al. |
| 7,766,929 B2 | 8/2010 | Masuda |
| 7,770,722 B2 | 8/2010 | Donahoe et al. |
| 7,770,775 B2 | 8/2010 | Shelton, IV et al. |
| 7,776,037 B2 | 8/2010 | Odom |
| 7,780,660 B2 | 8/2010 | Bourne et al. |
| 7,802,121 B1 | 9/2010 | Zansky et al. |
| 7,815,658 B2 | 10/2010 | Murakami |
| 7,845,537 B2 | 12/2010 | Shelton, IV et al. |
| 7,846,155 B2 | 12/2010 | Houser et al. |
| 7,846,159 B2 | 12/2010 | Morrison et al. |
| 7,889,489 B2 | 2/2011 | Richardson et al. |
| 7,918,848 B2 | 4/2011 | Lau et al. |
| 7,922,063 B2 | 4/2011 | Zemlok et al. |
| 7,923,151 B2 | 4/2011 | Lam et al. |
| 7,948,208 B2 | 5/2011 | Partovi et al. |
| 7,952,322 B2 | 5/2011 | Partovi et al. |
| 7,952,873 B2 | 5/2011 | Glahn et al. |
| 7,959,050 B2 | 6/2011 | Smith et al. |
| 7,977,921 B2 | 7/2011 | Bahai et al. |
| 7,982,439 B2 | 7/2011 | Trainor et al. |
| 8,038,025 B2 | 10/2011 | Stark et al. |
| 8,040,107 B2 | 10/2011 | Ishii |
| 8,052,605 B2 | 11/2011 | Muller et al. |
| 8,058,771 B2 | 11/2011 | Giordano et al. |
| 8,075,530 B2 | 12/2011 | Taylor et al. |
| 8,097,011 B2 | 1/2012 | Hideo et al. |
| 8,142,461 B2 | 3/2012 | Houser et al. |
| 8,147,488 B2 | 4/2012 | Masuda |
| 8,177,776 B2 | 5/2012 | Humayun et al. |
| 8,179,103 B2 | 5/2012 | Doljack |
| 8,195,271 B2 | 6/2012 | Rahn |
| 8,210,411 B2 | 7/2012 | Yates et al. |
| 8,216,212 B2 | 7/2012 | Grant et al. |
| 8,221,418 B2 | 7/2012 | Prakash et al. |
| 8,240,498 B2 | 8/2012 | Ramsey et al. |
| 8,246,642 B2 | 8/2012 | Houser et al. |
| 8,251,994 B2 | 8/2012 | McKenna et al. |
| 8,267,094 B2 | 9/2012 | Danek et al. |
| 8,277,446 B2 | 10/2012 | Heard |
| 8,292,882 B2 | 10/2012 | Danek et al. |
| 8,292,888 B2 | 10/2012 | Whitman |
| 8,298,253 B2 | 10/2012 | Charles |
| 8,301,262 B2 | 10/2012 | Mi et al. |
| 8,323,271 B2 | 12/2012 | Humayun et al. |
| 8,328,732 B2 | 12/2012 | Parihar et al. |
| 8,328,802 B2 | 12/2012 | Deville et al. |
| 8,333,764 B2 | 12/2012 | Francischelli et al. |
| 8,336,725 B2 | 12/2012 | Ramsey et al. |
| 8,337,097 B2 | 12/2012 | Cao |
| 8,344,690 B2 | 1/2013 | Smith et al. |
| 8,372,099 B2 | 2/2013 | Deville et al. |
| 8,377,059 B2 | 2/2013 | Deville et al. |
| 8,400,108 B2 | 3/2013 | Powell et al. |
| 8,403,948 B2 | 3/2013 | Deville et al. |
| 8,403,949 B2 | 3/2013 | Palmer et al. |
| 8,403,950 B2 | 3/2013 | Palmer et al. |
| 8,419,757 B2 | 4/2013 | Smith et al. |
| 8,425,545 B2 | 4/2013 | Smith et al. |
| 8,444,653 B2 | 5/2013 | Nycz et al. |
| 8,444,662 B2 | 5/2013 | Palmer et al. |
| 8,449,529 B2 | 5/2013 | Bek et al. |
| 8,459,520 B2 | 6/2013 | Giordano et al. |
| 8,461,744 B2 | 6/2013 | Wiener et al. |
| 8,487,487 B2 | 7/2013 | Dietz et al. |
| 8,522,795 B2 | 9/2013 | Bouix et al. |
| 8,550,106 B2 | 10/2013 | Hebach et al. |
| 8,550,981 B2 | 10/2013 | Woodruff et al. |
| 8,551,088 B2 | 10/2013 | Falkenstein et al. |
| 8,564,242 B2 | 10/2013 | Hansford et al. |
| 8,573,461 B2 | 11/2013 | Shelton, IV et al. |
| 8,598,852 B2 | 12/2013 | Gilmore |
| 8,602,287 B2 | 12/2013 | Yates et al. |
| 8,608,045 B2 | 12/2013 | Smith et al. |
| 8,617,077 B2 | 12/2013 | van Groningen et al. |
| 8,622,274 B2 | 1/2014 | Yates et al. |
| 8,623,027 B2 | 1/2014 | Price et al. |
| 8,632,535 B2 | 1/2014 | Shelton, IV et al. |
| 8,636,736 B2 | 1/2014 | Yates et al. |
| 8,641,629 B2 | 2/2014 | Kurokawa |
| 8,657,174 B2 | 2/2014 | Yates et al. |
| 8,663,112 B2 | 3/2014 | Slayton et al. |
| 8,733,614 B2 | 5/2014 | Ross et al. |
| 8,758,342 B2 | 6/2014 | Bales et al. |
| 8,784,415 B2 | 7/2014 | Malackowski et al. |
| 8,808,319 B2 | 8/2014 | Houser et al. |

(56) References Cited

U.S. PATENT DOCUMENTS

| | | |
|---|---|---|
| 8,834,465 B2 | 8/2014 | Ramstein et al. |
| 8,864,761 B2 | 10/2014 | Johnson et al. |
| 8,906,017 B2 | 12/2014 | Rioux et al. |
| 8,939,974 B2 | 1/2015 | Boudreaux et al. |
| 8,961,441 B2 | 2/2015 | Cioanta et al. |
| 8,968,648 B2 | 3/2015 | Kaneko |
| 8,986,302 B2 | 3/2015 | Aldridge et al. |
| 8,998,939 B2 | 4/2015 | Price et al. |
| 9,000,720 B2 | 4/2015 | Stulen et al. |
| 9,011,336 B2 | 4/2015 | Slayton et al. |
| 9,011,427 B2 | 4/2015 | Price et al. |
| 9,011,471 B2 | 4/2015 | Timm et al. |
| 9,017,849 B2 | 4/2015 | Stulen et al. |
| 9,017,851 B2 | 4/2015 | Felder et al. |
| 9,023,071 B2 | 5/2015 | Miller et al. |
| 9,044,261 B2 | 6/2015 | Houser |
| 9,050,098 B2 | 6/2015 | Deville et al. |
| 9,050,125 B2 | 6/2015 | Boudreaux et al. |
| 9,060,750 B2 | 6/2015 | Lam |
| 9,072,523 B2 | 7/2015 | Houser et al. |
| 9,072,543 B2 | 7/2015 | Miller et al. |
| 9,078,671 B2 | 7/2015 | Beale et al. |
| 9,089,338 B2 | 7/2015 | Smith et al. |
| 9,039,720 B2 | 8/2015 | Madan |
| 9,095,346 B2 | 8/2015 | Houser et al. |
| 9,113,903 B2 | 8/2015 | Unger et al. |
| 9,161,803 B2 | 10/2015 | Yates et al. |
| 9,179,912 B2 | 11/2015 | Yates et al. |
| 9,186,046 B2 | 11/2015 | Ramamurthy et al. |
| 9,186,047 B2 | 11/2015 | Ramamurthy et al. |
| 9,192,428 B2 | 11/2015 | Houser et al. |
| 9,247,986 B2 | 2/2016 | Haberstich et al. |
| 9,308,009 B2 | 4/2016 | Madan et al. |
| 9,318,271 B2 | 4/2016 | Fletcher et al. |
| 9,364,279 B2 | 6/2016 | Houser et al. |
| 9,364,288 B2 | 6/2016 | Smith et al. |
| 9,375,255 B2 | 6/2016 | Houser et al. |
| 9,381,058 B2 | 7/2016 | Houser et al. |
| 9,408,575 B2 | 8/2016 | Bordoley et al. |
| 9,421,062 B2 | 8/2016 | Houser et al. |
| 9,441,954 B2 | 9/2016 | Ramamurthy et al. |
| 9,500,472 B2 | 11/2016 | Ramamurthy et al. |
| 9,500,473 B2 | 11/2016 | Ramamurthy et al. |
| 9,510,895 B2 | 12/2016 | Houser et al. |
| 9,529,921 B2 | 12/2016 | Kimball et al. |
| 9,597,143 B2 | 3/2017 | Madan et al. |
| 9,622,832 B2 | 4/2017 | Birkenbach et al. |
| 9,629,652 B2 | 4/2017 | Mumaw et al. |
| 9,649,150 B2 | 5/2017 | Houser et al. |
| 9,782,214 B2 | 10/2017 | Houser et al. |
| 2001/0032666 A1 | 10/2001 | Jenson et al. |
| 2002/0165577 A1 | 11/2002 | Witt et al. |
| 2003/0093103 A1 | 5/2003 | Malackowski et al. |
| 2003/0109802 A1 | 6/2003 | Laeseke et al. |
| 2003/0114851 A1 | 6/2003 | Truckai et al. |
| 2003/0144680 A1 | 7/2003 | Kellogg et al. |
| 2003/0214270 A1* | 11/2003 | Shiue ............... H03K 3/53 320/166 |
| 2004/0097911 A1 | 5/2004 | Murakami et al. |
| 2004/0116952 A1 | 6/2004 | Sakurai et al. |
| 2004/0133189 A1 | 7/2004 | Sakurai |
| 2004/0173487 A1 | 9/2004 | Johnson et al. |
| 2005/0021065 A1 | 1/2005 | Yamada et al. |
| 2005/0033195 A1 | 2/2005 | Fulton, III et al. |
| 2005/0171522 A1 | 8/2005 | Christopherson |
| 2005/0203546 A1 | 9/2005 | Van Wyk et al. |
| 2006/0030797 A1 | 2/2006 | Zhou et al. |
| 2006/0079829 A1 | 4/2006 | Fulton, III et al. |
| 2006/0079874 A1 | 4/2006 | Faller et al. |
| 2006/0079877 A1 | 4/2006 | Houser et al. |
| 2006/0079879 A1 | 4/2006 | Faller et al. |
| 2006/0253176 A1 | 11/2006 | Caruso et al. |
| 2007/0027447 A1 | 2/2007 | Theroux et al. |
| 2007/0103437 A1 | 5/2007 | Rosenberg |
| 2007/0191713 A1 | 8/2007 | Eichmann et al. |
| 2007/0207354 A1 | 9/2007 | Curello et al. |
| 2007/0261978 A1 | 11/2007 | Sanderson |
| 2007/0265613 A1 | 11/2007 | Edelstein et al. |
| 2007/0265620 A1 | 11/2007 | Kraas et al. |
| 2007/0282333 A1 | 12/2007 | Fortson et al. |
| 2008/0003491 A1 | 1/2008 | Yahnker et al. |
| 2008/0004656 A1 | 1/2008 | Livneh |
| 2008/0057470 A1 | 3/2008 | Levy et al. |
| 2008/0147058 A1 | 6/2008 | Horrell et al. |
| 2008/0150754 A1 | 6/2008 | Quendt |
| 2008/0164842 A1 | 7/2008 | Bergner |
| 2008/0173651 A1 | 7/2008 | Ping |
| 2008/0188810 A1 | 8/2008 | Larsen et al. |
| 2008/0200940 A1 | 8/2008 | Eichmann et al. |
| 2008/0228104 A1 | 9/2008 | Uber, III et al. |
| 2008/0255413 A1 | 10/2008 | Zemlok et al. |
| 2008/0281301 A1 | 11/2008 | Deboer et al. |
| 2008/0315829 A1* | 12/2008 | Jones ............... H02J 7/345 320/103 |
| 2009/0030437 A1 | 1/2009 | Houser et al. |
| 2009/0043797 A1 | 2/2009 | Dorie et al. |
| 2009/0076506 A1 | 3/2009 | Baker |
| 2009/0096430 A1 | 4/2009 | Van Der Linde et al. |
| 2009/0143799 A1 | 6/2009 | Smith et al. |
| 2009/0143800 A1 | 6/2009 | Deville et al. |
| 2009/0209990 A1* | 8/2009 | Yates ............... A61B 17/07207 606/169 |
| 2009/0253030 A1 | 10/2009 | Kooij |
| 2009/0281430 A1 | 11/2009 | Wilder |
| 2010/0021022 A1 | 1/2010 | Pittel et al. |
| 2010/0030218 A1 | 2/2010 | Prevost |
| 2010/0060231 A1 | 3/2010 | Trainor et al. |
| 2010/0106144 A1 | 4/2010 | Matsumura et al. |
| 2010/0106146 A1 | 4/2010 | Boitor et al. |
| 2010/0125172 A1 | 5/2010 | Jayaraj |
| 2010/0152610 A1 | 6/2010 | Parihar et al. |
| 2010/0201311 A1 | 8/2010 | Alexander et al. |
| 2010/0249665 A1 | 9/2010 | Roche |
| 2010/0268221 A1 | 10/2010 | Beller et al. |
| 2010/0274160 A1 | 10/2010 | Yachi et al. |
| 2011/0009694 A1 | 1/2011 | Schultz et al. |
| 2011/0074336 A1 | 3/2011 | Miller |
| 2011/0077514 A1 | 3/2011 | Ulric et al. |
| 2011/0080134 A1 | 4/2011 | Miller |
| 2011/0221398 A1 | 9/2011 | Ferber, Jr. |
| 2012/0111591 A1 | 5/2012 | Shelton, IV et al. |
| 2012/0116260 A1 | 5/2012 | Johnson et al. |
| 2012/0116261 A1 | 5/2012 | Mumaw et al. |
| 2012/0116262 A1 | 5/2012 | Houser et al. |
| 2012/0116263 A1 | 5/2012 | Houser et al. |
| 2012/0116265 A1 | 5/2012 | Houser et al. |
| 2012/0116266 A1 | 5/2012 | Houser et al. |
| 2012/0116381 A1 | 5/2012 | Houser et al. |
| 2012/0179036 A1 | 7/2012 | Patrick et al. |
| 2012/0292367 A1 | 11/2012 | Morgan et al. |
| 2012/0305427 A1 | 12/2012 | Felder et al. |
| 2013/0085330 A1 | 4/2013 | Ramamurthy et al. |
| 2013/0090528 A1 | 4/2013 | Ramamurthy et al. |
| 2013/0118733 A1 | 5/2013 | Kumar |
| 2014/0088379 A1 | 3/2014 | Bhamra et al. |
| 2015/0305763 A1 | 10/2015 | Houser et al. |
| 2016/0121143 A1 | 5/2016 | Mumaw et al. |
| 2016/0206900 A1 | 7/2016 | Haberstich et al. |
| 2016/0329614 A1 | 11/2016 | Madan et al. |
| 2016/0338760 A1 | 11/2016 | Houser et al. |
| 2017/0042569 A1 | 2/2017 | Houser et al. |

FOREIGN PATENT DOCUMENTS

| | | |
|---|---|---|
| EP | 0897696 A1 | 2/1999 |
| EP | 0947167 A1 | 10/1999 |
| EP | 1330991 A1 | 7/2003 |
| EP | 1525853 A2 | 4/2005 |
| EP | 1535585 A2 | 6/2005 |
| EP | 1684396 A2 | 7/2006 |
| EP | 1721576 A1 | 11/2006 |
| EP | 1743592 A1 | 1/2007 |
| EP | 1818021 A1 | 8/2007 |
| EP | 1839599 | 10/2007 |

(56) References Cited

FOREIGN PATENT DOCUMENTS

| | | |
|---|---|---|
| EP | 1868275 A2 | 12/2007 |
| EP | 1886637 A1 | 2/2008 |
| EP | 1943976 A2 | 7/2008 |
| EP | 1970014 | 9/2008 |
| EP | 2027819 A1 | 2/2009 |
| EP | 2090256 A2 | 8/2009 |
| EP | 2105104 A2 | 9/2009 |
| EP | 1997439 A2 | 12/2009 |
| EP | 2165660 A2 | 3/2010 |
| EP | 2218409 A1 | 8/2010 |
| EP | 2243439 A1 | 10/2010 |
| EP | 2345454 A1 | 7/2011 |
| GB | 2425874 | 11/2006 |
| GB | 2440566 A | 2/2008 |
| JP | H01-268370 | 10/1989 |
| JP | H10-308907 | 11/1998 |
| JP | 2002-336265 | 11/2002 |
| JP | 2005-033868 | 2/2005 |
| JP | 2010-518978 | 6/2010 |
| JP | 5410110 B | 2/2014 |
| WO | WO 1997/024072 | 7/1997 |
| WO | WO 2000/065682 | 2/2000 |
| WO | WO 2003/013374 | 2/2003 |
| WO | WO 2003/020139 | 3/2003 |
| WO | WO 2004/113991 | 12/2004 |
| WO | WO 2005/079915 | 9/2005 |
| WO | WO 2006/023266 | 3/2006 |
| WO | WO 2007/004515 | 1/2007 |
| WO | WO 2007/024983 | 3/2007 |
| WO | WO 2007/050439 | 5/2007 |
| WO | WO 2007/090025 | 8/2007 |
| WO | WO 2007/137115 | 11/2007 |
| WO | WO 2017/137304 A2 | 11/2007 |
| WO | WO-2007137304 A2 * 11/2007 ........... A61B 17/072 |
| WO | WO 2008/071898 | 6/2008 |
| WO | WO 2008/102154 | 8/2008 |
| WO | WO 2008/107902 | 9/2008 |
| WO | WO 2008/131357 | 10/2008 |
| WO | WO 2009/018409 | 2/2009 |
| WO | WO 2009/046394 | 4/2009 |
| WO | WO 2009/070780 | 6/2009 |
| WO | WO 2009/073608 | 6/2009 |
| WO | WO 2010/030850 | 3/2010 |
| WO | WO 2010/096174 | 8/2010 |
| WO | WO 2011/059785 | 5/2011 |
| WO | WO 2011/089270 | 7/2011 |

OTHER PUBLICATIONS

Dietz, T. et al., Partially Implantable Vibrating Ossicular Prosthesis, Transducers'97, vol. 1, International Conference on Solid State Sensors and Actuators, (Jun. 16-19, 1997) pp. 433-436 (Abstract).
"System 6 Aseptic Battery System," Stryker (2006) pp. 1-2.
Chinese Office Action dated Jan. 29, 2015 for Application No. CN 2011800640106.
Chinese Office Action dated Aug. 28, 2015 for Application No. CN 2011800640106.
Chinese Office Action dated Feb. 2, 2015 for Application No. CN 2011800534501.
Chinese Office Action dated Apr. 20, 2015 for Application No. CN 201180053434.2.
Chinese Search Report dated Oct. 8, 2016 for Application No. CN 201180053434.2.
Chinese Office Action dated Oct. 17, 2016 for Application No. CN 201180053434.2.
EP Communication dated Feb. 19, 2014 for Application No. EP 11781972.2.
International Search Report and Written Opinion dated Jan. 26, 2012 for Application No. PCT/US2011/059212.
International Preliminary Report on Patentability dated May 7, 2013 for Application No. PCT/US2011/059212.
Communication from the International Searching Authority dated Jan. 24, 2012 for Application No. PCT/US2011/059215.
International Search Report dated Apr. 4, 2012 for Application No. PCT/US2011/059215.
International Preliminary Report on Patentability dated May 8, 2013 for Application No. PCT/US2011/059215.
International Search Report dated Feb. 13, 2012 for Application No. PCT/US2011/059217.
International Preliminary Report on Patentability dated May 7, 2013 for Application No. PCT/US2011/059217.
International Search Report dated Jun. 12, 2012 for Application No. PCT/US2011/059218.
International Preliminary Report on Patentability dated May 7, 2013 for Application No. PCT/US2011/059218.
International Search Report dated Jan. 26, 2012 for Application No. PCT/US2011/059220.
International Preliminary Report on Patentability dated May 7, 2013 for Application No. PCT/US2011/059220.
Communication from the International Searching Authority dated Feb. 2, 2012 for Application No. PCT/US2011/059222.
International Search Report dated Apr. 18, 2012 for Application No. PCT/US2011/059222.
International Preliminary Report on Patentability dated May 7, 2013 for Application No. PCT/US2011/059222.
International Search Report dated Feb. 1, 2012 for Application No. PCT/US2011/059223.
International Preliminary Report on Patentability dated Feb. 1, 2012 for Application No. PCT/US2011/059223.
International Search Report dated Jan. 12, 2012 for Application No. PCT/US2011/059226.
International Preliminary Report on Patentability dated May 7, 2013 for Application No. PCT/US2011/059226.
International Search Report dated Mar. 15, 2012 for Application No. PCT/US2011/059338.
International Preliminary Report on Patentability dated May 7, 2013 for Application No. PCT/US2011/059338.
International Search Report dated Feb. 7, 2012 for Application No. PCT/US2011/059351.
International Preliminary Report on Patentability dated May 7, 2013 for Application No. PCT/US2011/059351.
International Search Report dated Feb. 2, 2012 for Application No. PCT/US2011/059354.
International Preliminary Report on Patentability dated May 7, 2013 for Application No. PCT/US2011/059354.
International Search Report dated May 29, 2012 for Application No. PCT/US2011/059358.
International Preliminary Report on Patentability dated May 7, 2013 for Application No. PCT/US2011/059358.
Communication from the International Searching Authority dated Feb. 6, 2012 for Application No. PCT/US2011/059362.
International Search Report dated Mar. 22, 2012 for Application No. PCT/US2011/059362.
International Preliminary Report on Patentability dated May 7, 2013 for Application No. PCT/US2011/059362.
International Search Report dated Jun. 4, 2012 for Application No. PCT/US2011/059365.
International Preliminary Report on Patentability dated May 8, 2013 for Application No. PCT/US2011/059365.
International Search Report dated Feb. 23, 2012 for Application No. PCT/US2011/059371.
International Preliminary Report on Patentability dated May 7, 2013 for Application No. PCT/US2011/059371.
Communication from the International Searching Authority dated Feb. 2, 2012 for Application No. PCT/US2011/059378.
International Search Report dated May 24, 2012 for Application No. PCT/US2011/059378.
International Preliminary Report on Patentability and Written Opinion dated May 7, 2013 for Application No. PCT/US2011/059378.
International Search Report dated Apr. 11, 2012 for Application No. PCT/US2011/059381.
International Search Report, revised, dated Jul. 6, 2012 for Application No. PCT/US2011/059381.
International Preliminary Report on Patentability and Written Opinion dated May 8, 2013 for Application No. PCT/US2011/059381.

(56) References Cited

OTHER PUBLICATIONS

Japanese Office Action, Notification of Reasons for Refusal, dated Sep. 1, 2015 for Application No. JP 2013-537837.
Japanese Office Action, Notification of Reasons for Refusal, dated Feb. 16, 2016 for Application No. JP 2013-537837.
Japanese Office Action, Pretrial Examination Report, dated Aug. 2, 2016 for Application No. JP 2013-537837.
Japanese Office Action, Notification of Reasons for Refusal, dated Sep. 1, 2015 for Application No. JP 2013-537866.
Japanese Office Action, Notification of Reasons for Refusal, dated Jun. 28, 2016 for Application No. JP 2013-537866.
Japanese Office Action, Notification of Reasons for Refusal, dated Oct. 6, 2015 for Application No. JP 2013-537869.
Japanese Office Action, Examiner's Decision of Refusal, dated Sep. 13, 2016 for Application No. JP 2013-537869.
U.S. Office Action, Non-Final, dated Aug. 6, 2013 for U.S. Appl. No. 13/151,471.
U.S. Office Action, Notice of Allowance, dated Dec. 6, 2013 for U.S. Appl. No. 13/151,471.
U.S. Office Action, Non-Final, dated Mar. 28, 2014 for U.S. Appl. No. 13/151,471.
U.S. Office Action, Notice of Allowance, dated Aug. 19, 2014 for U.S. Appl. No. 13/151,471.
U.S. Office Action, Notice of Allowance, dated Nov. 21, 2014 for U.S. Appl. No. 13/151,471.
U.S. Office Action, Restriction Requirement, dated Dec. 11, 2012 for U.S. Appl. No. 13/151,481.
U.S. Office Action, Non-Final, dated Feb. 15, 2013 for U.S. Appl. No. 13/151,481.
U.S. Office Action, Final, dated Jun. 7, 2013 for U.S. Appl. No. 13/151,481.
U.S. Office Action, Non-Final, dated Aug. 14, 2014 for U.S. Appl. No. 13/151,481.
U.S. Office Action, Restriction Requirement, dated Jul. 5, 2013 for U.S. Appl. No. 13/151,488.
U.S. Office Action, Non-Final, dated Nov. 7, 2014 for U.S. Appl. No. 13/151,488.
U.S. Office Action, Non-Final, dated Jun. 14, 2013 for U.S. Appl. No. 13/151,498.
U.S. Office Action, Final, dated Nov. 21, 2013 for U.S. Appl. No. 13/151,498.
U.S. Office Action, Non-Final, dated Mar. 18, 2014 for U.S. Appl. No. 13/151,498.
U.S. Office Action, Notice of Allowance, dated Aug. 6, 2014 for U.S. Appl. No. 13/151,498.
U.S. Office Action, Notice of Allowance, dated Nov. 21, 2014 for U.S. Appl. No. 13/151,498.
U.S. Office Action, Non-Final, dated Jun. 18, 2014 for U.S. Appl. No. 13/151,503.
U.S. Office Action, Non-Final, dated Nov. 6, 2014 for U.S. Appl. No. 13/151,503.
U.S. Office Action, Final, dated Jun. 8, 2015 for U.S. Appl. No. 13/151,503.
U.S. Office Action, Non-Final, dated Oct. 2, 2015 for U.S. Appl. No. 13/151,503.
U.S. Office Action, Final, dated Mar. 9, 2016 for U.S. Appl. No. 13/151,503.
U.S. Office Action, Notice of Allowance, dated Jul. 27, 2016 for U.S. Appl. No. 13/151,503.
U.S. Office Action, Restriction Requirement, dated Mar. 13, 2013 for U.S. Appl. No. 13/151,509.
U.S. Office Action, Restriction Requirement, dated Jun. 24, 2013 for U.S. Appl. No. 13/151,509.
U.S. Office Action, Non-Final, dated Sep. 26, 2013 for U.S. Appl. No. 13/151,509.
U.S. Office Action, Final, dated Jan. 29, 2014 for U.S. Appl. No. 13/151,509.
U.S. Office Action, Non-Final, dated Jul. 9, 2014 for U.S. Appl. No. 13/151,509.
U.S. Office Action, Notice of Allowance, dated Oct. 28, 2014 for U.S. Appl. No. 13/151,509.
U.S. Office Action, Restriction Requirement, dated Jun. 11, 2014 for U.S. Appl. No. 13/151,512.
U.S. Office Action, Notice of Allowance, dated Oct. 29, 2014 for U.S. Appl. No. 13/151,512.
U.S. Office Action, Restriction Requirement, dated Jul. 11, 2014 for U.S. Appl. No. 13/269,780.
U.S. Office Action, Restriction Requirement, dated Feb. 28, 2013 for U.S. Appl. No. 13/270,667.
U.S. Office Action, Non-Final, dated Apr. 26, 2013 for U.S. Appl. No. 13/270,667.
U.S. Office Action, Final, dated Oct. 25, 2013 for U.S. Appl. No. 13/270,667.
U.S. Office Action, Non-Final, dated Jul. 29, 2014 for U.S. Appl. No. 13/270,667.
U.S. Office Action, Notice of Allowance, dated Dec. 17, 2014 for U.S. Appl. No. 13/270,667.
U.S. Office Action, Restriction Requirement, dated Jul. 9, 2014 for U.S. Appl. No. 13/270,684.
U.S. Office Action, Non-Final, dated Oct. 9, 2014 for U.S. Appl. No. 13/270,684.
U.S. Office Action, Restriction Requirement, dated Sep. 11, 2014 for U.S. Appl. No. 13/270,701.
U.S. Office Action, Non-Final, dated Dec. 16, 2014 for U.S. Appl. No. 13/270,701.
U.S. Office Action, Non-Final, dated Nov. 21, 2013 for U.S. Appl. No. 13/271,352.
U.S. Office Action, Restriction Requirement, dated Sep. 25, 2014 for U.S. Appl. No. 13/271,352.
U.S. Office Action, Restriction Requirement, dated Oct. 2, 2013 for U.S. Appl. No. 13/274,480.
U.S. Office Action, Non-Final, dated Feb. 14, 2014 for U.S. Appl. No. 13/274,480.
U.S. Office Action, Final, dated Jul. 17, 2014 for U.S. Appl. No. 13/274,480.
U.S. Office Action, Restriction Requirement, dated Dec. 9, 2013 for U.S. Appl. No. 13/274,496.
U.S. Office Action, Non-Final, dated Feb. 6, 2014 for U.S. Appl. No. 13/274,496.
U.S. Office Action, Final, dated May 15, 2014 for U.S. Appl. No. 13/274,496.
U.S. Office Action, Final, dated Aug. 22, 2014 for U.S. Appl. No. 13/274,496.
U.S. Office Action, Restriction Requirement, dated Mar. 28, 2014 for U.S. Appl. No. 13/274,507.
U.S. Office Action, Non-Final, dated Jun. 19, 2014 for U.S. Appl. No. 13/274,507.
U.S. Office Action, Non-Final, dated Dec. 21, 2012 for U.S. Appl. No. 13/274,516.
U.S. Office Action, Final, dated Aug. 16, 2013 for U.S. Appl. No. 13/274,516.
U.S. Office Action, Non-Final, dated Dec. 6, 2013 for U.S. Appl. No. 13/274,516.
U.S. Office Action, Final, dated Jun. 12, 2014 for U.S. Appl. No. 13/274,516.
U.S. Office Action, Non-Final, dated Oct. 8, 2014 for U.S. Appl. No. 13/274,516.
U.S. Office Action, Restriction Requirement, dated Feb. 25, 2013 for U.S. Appl. No. 13/274,540.
U.S. Office Action, Non-Final, dated Apr. 30, 2013 for U.S. Appl. No. 13/274,540.
U.S. Office Action, Final, dated Oct. 25, 2013 for U.S. Appl. No. 13/274,540.
U.S. Office Action, Non-Final, dated Aug. 26, 2014 for U.S. Appl. No. 13/274,540.
U.S. Office Action, Non-Final, dated Apr. 1, 2013 for U.S. Appl. No. 13/274,805.
U.S. Office Action, Final, dated Sep. 12, 2013 for U.S. Appl. No. 13/274,805.
U.S. Office Action, Non-Final, dated Aug. 14, 2014 for U.S. Appl. No. 13/274,805.

(56) References Cited

OTHER PUBLICATIONS

U.S. Office Action, Notice of Allowance, dated Nov. 28, 2014 for U.S. Appl. No. 13/274,805.
U.S. Office Action, Restriction Requirement, dated Apr. 29, 2013 for U.S. Appl. No. 13/274,830.
U.S. Office Action, Non-Final, dated Jun. 14, 2013 for U.S. Appl. No. 13/274,830.
U.S. Office Action, Final, dated Nov. 26, 2013 for U.S. Appl. No. 13/274,830.
U.S. Office Action, Non-Final, dated Oct. 22, 2014 for U.S. Appl. No. 13/274,830.
U.S. Office Action, Non-Final, dated Jan. 6, 2014 for U.S. Appl. No. 13/275,514.
U.S. Office Action, Non-Final, dated Sep. 9, 2014 for U.S. Appl. No. 13/275,514.
U.S. Office Action, Non-Final, dated May 21, 2015 for U.S. Appl. No. 13/275,514.
U.S. Office Action, Final, dated Sep. 11, 2015 for U.S. Appl. No. 13/275,514.
U.S. Office Action, Notice of Allowance, dated Nov. 25, 2015 for U.S. Appl. No. 13/275,514.
U.S. Office Action, Notice of Allowance, dated Mar. 2, 2016 for U.S. Appl. No. 13/275,514.
U.S. Office Action, Non-Final, dated May 17, 2013 for U.S. Appl. No. 13/275,547.
U.S. Office Action, Final, dated Feb. 28, 2014 for U.S. Appl. No. 13/275,547.
U.S. Office Action, Non-Final, dated Aug. 20, 2014 for U.S. Appl. No. 13/275,547.
U.S. Office Action, Final, dated Mar. 10, 2015 for U.S. Appl. No. 13/275,547.
U.S. Office Action, Non-Final, dated Aug. 28, 2015 for U.S. Appl. No. 13/275,547.
U.S. Office Action, Final, dated May 6, 2016 for U.S. Appl. No. 13/275,547.
U.S. Office Action, Non-Final, dated Feb. 1, 2013 for U.S. Appl. No. 13/275,563.
U.S. Office Action, Final, dated Aug. 29, 2013 for U.S. Appl. No. 13/275,563.
U.S. Office Action, Non-Final, dated Oct. 23, 2014 for U.S. Appl. No. 13/275,563.
U.S. Office Action, Restriction Requirement, dated Feb. 6, 2013 for U.S. Appl. No. 13/276,660.
U.S. Office Action, Non-Final, dated Jun. 3, 2013 for U.S. Appl. No. 13/276,660.
U.S. Office Action, Restriction Requirement, dated Jul. 9, 2014 for U.S. Appl. No. 13/276,660.
U.S. Office Action, Non-Final, dated Dec. 21, 2012 for U.S. Appl. No. 13/276,673.
U.S. Office Action, Non-Final, dated Aug. 19, 2013 for U.S. Appl. No. 13/276,673.
U.S. Office Action, Final, dated Mar. 21, 2014 for U.S. Appl. No. 13/276,673.
U.S. Office Action, Non-Final, dated Aug. 14, 2014 for U.S. Appl. No. 13/276,673.
U.S. Office Action, Restriction Requirement, dated Feb. 6, 2013 for U.S. Appl. No. 13/276,687.
U.S. Office Action, Non-Final, dated Jun. 12, 2013 for U.S. Appl. No. 13/276,687.
U.S. Office Action, Notice of Allowance, dated Nov. 12, 2013 for U.S. Appl. No. 13/276,687.
U.S. Office Action, Notice of Allowance, dated Jun. 2, 2014 for U.S. Appl. No. 13/276,687.
U.S. Office Action, Notice of Allowance, dated Sep. 12, 2014 for U.S. Appl. No. 13/276,687.
U.S. Office Action, Restriction Requirement, dated Feb. 21, 2013 for U.S. Appl. No. 13/276,707.
U.S. Office Action, Non-Final, dated May 6, 2013 for U.S. Appl. No. 13/276,707.
U.S. Office Action, Final, dated Sep. 27, 2013 for U.S. Appl. No. 13/276,707.
U.S. Office Action, Restriction Requirement, dated Feb. 6, 2013 for U.S. Appl. No. 13/276,725.
U.S. Office Action, Non-Final, dated Aug. 20, 2014 for U.S. Appl. No. 13/276,725.
U.S. Office Action, Restriction Requirement, dated Dec. 21, 2012 for U.S. Appl. No. 13/276,745.
U.S. Office Action, Non-Final, dated Feb. 28, 2014 for U.S. Appl. No. 13/276,745.
U.S. Office Action, Notice of Allowance, dated Oct. 7, 2014 for U.S. Appl. No. 13/276,745.
U.S. Office Action, Notice of Allowance, dated Dec. 19, 2014 for U.S. Appl. No. 13/276,745.
U.S. Office Action, Non-Final, dated Apr. 30, 2013 for U.S. Appl. No. 13/276,745.
U.S. Office Action, Final, dated Nov. 8, 2013 for U.S. Appl. No. 13/276,745.
U.S. Office Action, Restriction Requirement, dated Sep. 24, 2014 for U.S. Appl. No. 13/277,328.
U.S. Office Action, Non-Final, dated Dec. 8, 2014 for U.S. Appl. No. 13/277,328.
Machine Translation of the Abstract of German Application No. DE 102009013034.
Machine Translation of German Application No. DE 102008051866.
Indian Office Action, Examination Report, dated Jun. 13, 2019 for Application No. 3973/DELNP/2013, 6 pgs.
U.S. Office Action, Notice of Allowance, dated Nov. 2, 2016 for U.S. Appl. No. 13/151,503.
U.S. Office Action, Restriction Requirement, dated Apr. 4, 2013 for U.S. Appl. No. 13/275,495.
U.S. Office Action, Non-Final, dated May 31, 2013 for U.S. Appl. No. 13/275,495.
U.S. Office Action, Final, dated Dec. 5, 2013 for U.S. Appl. No. 13/275,495.
U.S. Office Action, Non-Final, dated Feb. 25, 2015 for U.S. Appl. No. 13/275,495.
U.S. Office Action, Final, dated May 27, 2015 for U.S. Appl. No. 13/275,495.
U.S. Office Action, Non-Final, dated Jun. 6, 2016 for U.S. Appl. No. 13/275,495.
U.S. Office Action, Final, dated Dec. 21, 2016 for U.S. Appl. No. 13/275,495.

* cited by examiner

SURGICAL INSTRUMENT WITH CHARGING DEVICES

PRIORITY

This application is a divisional of application Ser. No. 13/275,495, filed on Oct. 18, 2011, entitled "Surgical Instrument with Charging Devices," published as U.S. Pub. No. 2012/0116265 on May 10, 2012, now abandoned, the disclosure of which is incorporated herein and which claims priority to U.S. Provisional Application Ser. No. 61/410,603, filed Nov. 5, 2010, entitled "Energy-Based Surgical Instruments," the disclosure of which is incorporated by reference herein. Application Ser. No. 13/275,495 also claims priority to U.S. Provisional Application Ser. No. 61/487,846, filed May 19, 2011, entitled "Energy-Based Surgical Instruments," the disclosure of which is incorporated by reference herein.

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through a cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient.

Examples of endoscopic surgical instruments include those disclosed in U.S. Pat. Pub. No. 2006/0079874, entitled "Tissue Pad for Use with an Ultrasonic Surgical Instrument," published Apr. 13, 2006, now abandoned, the disclosure of which is incorporated by reference herein; U.S. Pat. Pub. No. 2007/0191713, entitled "Ultrasonic Device for Cutting and Coagulating," published Aug. 16, 2007, now abandoned, the disclosure of which is incorporated by reference herein; U.S. Pat. Pub. No. 2007/0282333, entitled "Ultrasonic Waveguide and Blade," published Dec. 6, 2007, now abandoned, the disclosure of which is incorporated by reference herein; U.S. Pat. Pub. No. 2008/0200940, entitled "Ultrasonic Device for Cutting and Coagulating," published Aug. 21, 2008, now abandoned, the disclosure of which is incorporated by reference herein; U.S. Pat. Pub. No. 2011/0015660, entitled "Rotating Transducer Mount for Ultrasonic Surgical Instruments," published Jan. 20, 2011, and issued Jun. 11, 2013 as U.S. Pat. No. 8,461,744, the disclosure of which is incorporated by reference herein; U.S. Pat. No. 6,500,176, entitled "Electrosurgical Systems and Techniques for Sealing Tissue," issued Dec. 31, 2002, the disclosure of which is incorporated by reference herein; and U.S. Pat. Pub. No. 2011/0087218, entitled "Surgical Instrument Comprising First and Second Drive Systems Actuatable by a Common Trigger Mechanism," published Apr. 14, 2011, issued as U.S. Pat. No. 8,939,974 on Jan. 27, 2015, the disclosure of which is incorporated by reference herein. Additionally, such surgical tools may include a cordless transducer such as that disclosed in U.S. Pat. Pub. No. 2009/0143797, entitled "Cordless Hand-held Ultrasonic Cautery Cutting Device," published Jun. 4, 2009, and issued Apr. 16, 2013 as U.S. Pat. No. 8,419,757, the disclosure of which is incorporated by reference herein. In addition, the surgical instruments may be used, or adapted for use, in robotic-assisted surgery settings such as that disclosed in U.S. Pat. No. 6,783,524, entitled "Robotic Surgical Tool with Ultrasound Cauterizing and Cutting Instrument," issued Aug. 31, 2004, the disclosure of which is incorporated by reference herein.

While several systems and methods have been made and used for surgical instruments, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

Figure 1:
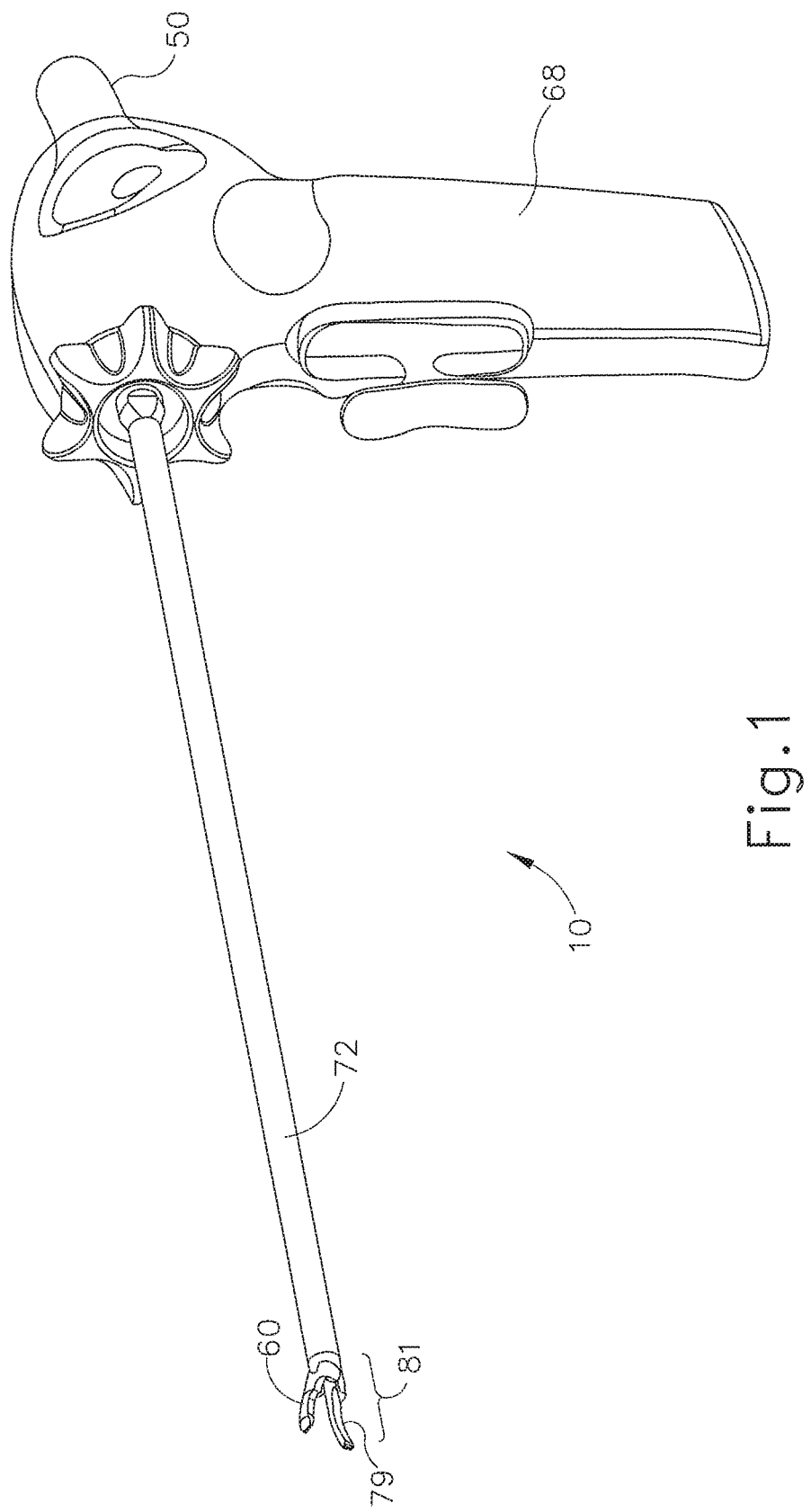
FIG. 1 depicts perspective view of an exemplary surgical instrument.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

Various examples described herein are directed to improved ultrasonic surgical instruments configured for effecting tissue dissecting, cutting, and/or coagulation during surgical procedures. For example, the teachings herein may be readily combined with various teachings from any of the following, in numerous ways, as will be apparent to those of ordinary skill in the art: U.S. Pat. No. 7,738,971 entitled "Post-Sterilization Programming of Surgical Instruments," issued Jun. 15, 2010, the disclosure of which is incorporated by reference herein; U.S. Pub. No. 2006/0079874 entitled "Tissue Pad for Use with an Ultrasonic Surgical Instrument," published Apr. 13, 2006, now abandoned, the disclosure of which is incorporated by reference herein; U.S. Pub. No. 2007/0191713 entitled "Ultrasonic Device for Cutting and Coagulating," published Aug. 16, 2007, now abandoned, the disclosure of which is incorporated by reference herein; U.S. Pub. No. 2007/0282333 entitled "Ultrasonic Waveguide and Blade," published Dec. 6, 2007, now abandoned, the disclosure of which is incorporated by reference herein; U.S. Pub. No. 2008/0200940 entitled "Ultrasonic Device for Cutting and Coagulating," published Aug. 21, 2008, now abandoned, the disclosure of which is incorporated by reference herein; U.S. Pat. Pub. No. 2009/0143797, entitled "Cordless Hand-held Ultrasonic Cautery Cutting Device," published Jun. 4, 2009, and issued Apr. 16, 2013 as U.S. Pat. No. 8,419,757, the disclosure of which is incorporated by reference herein; U.S. Pub. No. 2009/0209990 entitled "Motorized Surgical Cutting and Fastening Instrument Having Handle Based Power Source," published Aug. 20, 2009, issued as U.S. Pat. No. 8,657,174 on Feb. 25, 2014, the disclosure of which is incorporated by reference herein; U.S. Pub. No. 2010/0069940 entitled "Ultrasonic Device for Fingertip Control," published Mar. 18, 2010, issued as U.S. Pat. No. 9,023,071 on May 5, 2015, the disclosure of which is incorporated by reference herein; and U.S. Pub. No. 2011/0015660, entitled "Rotating Transducer Mount for Ultrasonic Surgical Instruments," published Jan. 20, 2011, and issued Jun. 11, 2013 as U.S. Pat. No. 8,461,744, the disclosure of which is incorporated by reference herein. Similarly, various ways in which medical devices may be adapted to include a portable power source are disclosed in U.S. Provisional Application Ser. No. 61/410,603, filed Nov. 5, 2010, entitled "Energy-Based Surgical Instruments," the disclosure of which is incorporated by reference herein.

As will become apparent from the following description, it is contemplated that versions of the surgical instrument described herein may be used in association with an oscillator module of a surgical system, whereby ultrasonic energy from the oscillator module provides the desired ultrasonic actuation for the present surgical instrument. It is also contemplated that versions of the surgical instrument described herein may be used in association with a signal generator module of a surgical system, whereby electrical energy in the form of radio frequencies (RF), for example, is used to provide feedback to the user regarding the surgical instrument. The ultrasonic oscillator and/or the signal generator modules may be non-detachably integrated with the surgical instrument or may be provided as separate components, which can be electrically attachable to the surgical instrument.

It should also be understood that the teachings herein may be readily applied to various types of electrosurgical instruments, including but not limited to those taught in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein; U.S. Pub. No. 2011/0087218, entitled "Surgical Instrument Comprising First and Second Drive Systems Actuatable by a Common Trigger Mechanism," published Apr. 14, 2011, issued as U.S. Pat. No. 8,939,974 on Jan. 27, 2015, the disclosure of which is incorporated by reference herein; and U.S. patent application Ser. No. 13/151,481, entitled "Motor Driven Electrosurgical Device with Mechanical and Electrical Feedback," filed Jun. 2, 2011, and issued on Oct. 20, 2015 as U.S. Pat. No. 9,161,803, the disclosure of which is incorporated by reference herein.

Furthermore, the teachings herein may be readily applied to various types of electrically powered cutting and stapling instruments, including but not limited to those taught in U.S. Pat. No. 7,416,101 entitled "Motor-Driven Surgical Cutting and Fastening Instrument with Loading Force Feedback," issued Aug. 26, 2008, the disclosure of which is incorporated by reference herein; U.S. Pub. No. 2009/0209979, entitled "Motorized Cutting and Fastening Instrument Having Control Circuit for Optimizing Battery Usage," published Aug. 20, 2009, issued as U.S. Pat. No. 8,622,274 on Jan. 7, 2014; and U.S. patent application Ser. No. 13/151,481, entitled "Motor Driven Electrosurgical Device with Mechanical and Electrical Feedback," filed Jun. 2, 2011, and issued on Oct. 20, 2015 as U.S. Pat. No. 9,161,803, the disclosure of which is incorporated by reference herein. Still other suitable types of devices to which the teachings herein may be applied will be apparent to those of ordinary skill in the art.

In view of the foregoing, it should be understood that the surgical instrument is not limited in its application or use to the details of construction and arrangement of parts illustrated in the accompanying drawings and description. The illustrative versions of the surgical instrument may be implemented or incorporated in other versions, variations and modifications, and may be practiced or carried out in various ways. Further, unless otherwise indicated, the terms and expressions employed herein have been chosen for the purpose of describing the illustrative versions of the present surgical instrument for the convenience of the reader and are not for the purpose of limiting the surgical instrument.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Exemplary Ultrasonic Instrument

The examples described herein relate to a battery powered ultrasonic surgical clamp coagulator apparatus which is configured for effecting tissue cutting, coagulation, and/or clamping during surgical procedures. When ultrasonic components of the apparatus are inactive, tissue can be readily gripped and manipulated, as desired, without tissue cutting. When the ultrasonic components are activated, the apparatus permits tissue to be gripped for coupling with the ultrasonic energy to effect tissue coagulation, with application of increased pressure efficiently effecting tissue cutting and coagulation. If desired, ultrasonic energy can be applied to tissue without use of the clamping mechanism of the apparatus by appropriate manipulation of the ultrasonic blade.

FIG. 1 shows a version of a surgical instrument (10). The surgical instrument (10) includes a battery connected to a control module as will be discussed in further detail below. Surgical instrument (10) further comprises an ultrasonic transducer (50). It will be noted that, in some applications, ultrasonic transducer (50) is referred to as a "hand piece assembly" because surgical instrument (10) is configured such that a surgeon may grasp and manipulate ultrasonic transducer (50) during various procedures and operations. Of course, instrument (10) may be configured for robotic manipulation in addition to or in lieu of human operator manipulation. Ultrasonic transducer (50) may be a disposable component, completely enclosed by instrument (10) and/or it may be a reusable component that is detachable from instrument (10). It will be appreciated that surgical instrument (10) may comprise any suitable combination of disposable components and reusable components.

Ultrasonic surgical instrument (10) further includes a multi-piece handle assembly (68) adapted to isolate the operator from the vibrations of the acoustic assembly contained within transducer (50). Handle assembly (68) may be shaped to be held by a user in a pistol-grip manner, but it is contemplated that instrument (10) may be grasped and manipulated in any other suitable manner as would be apparent to one of ordinary skill in the art in view of the teachings herein. While multi-piece handle assembly (68) is illustrated, handle assembly (68) may instead comprise a single unitary piece. Ultrasonic transducer (50) may also be attached to and removed from ultrasonic surgical instrument (10) as a unit. Handle assembly (68) may be constructed from a durable plastic, such as polycarbonate or a liquid crystal polymer. It is also contemplated that handle assembly (68) may alternatively be made from a variety of materials including other plastics, ceramics or metals.

Surgical instrument (10) further comprises an outer sheath (72) extending distally from handle assembly (68) leading to an end effector (81), which comprises clamp member (60) and blade (79). Clamp member (60) and blade (79) are operable to manipulate tissue in various ways as described herein. Ultrasonic transducer (50) is operable to deliver ultrasonic energy to end effector (81), which, in the exemplary version, is communicated from transducer (50) to end effector (81) through an acoustic waveguide (not shown) extending through outer sheath (72).

The distal end of blade (79) is disposed near an anti-node in order to tune the acoustic assembly to a preferred resonant frequency $f_o$ when the acoustic assembly is not loaded by tissue. When ultrasonic transducer (50) is energized, the distal end of blade (79) is configured to move longitudinally in the range of, for example, approximately 10 to 500 microns peak-to-peak, and preferably in the range of about 20 to about 200 microns at a predetermined vibrational frequency $f_o$ of, for example, 55,500 Hz. Thus, when tissue is secured between blade (79) and clamp arm (84), the ultrasonic oscillation of blade (79) may simultaneously sever tissue and denature the proteins in adjacent tissue cells, thereby providing a coagulative effect with relatively little thermal spread. An electrical current may also be provided through blade (79) and clamp arm (84) to cauterize the tissue. While some configurations for transducer (50) have been described, still other suitable configurations for transducer (50) will be apparent to one or ordinary skill in the art in view of the teachings herein.

A power supply is located inside the handle assembly (68) for providing power to the device including transducer (50). The power supply may include a primary battery, a rechargeable battery, a supercapacitor, a fuel cell or a combination of these or other means of supplying power. It should be understood that surgical instrument (10) may be constructed in accordance with some or all of the teachings of any of the references cited herein, including those relating to ultrasonic surgical instruments, those relating to RF electrosurgical instruments, or those relating to electrically powered cutting and stapling instruments. As another merely illustrative example, surgical instrument (10) may comprise a variation of the instruments described in any of the following: U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein; U.S. Pat. No. 5,938,633, entitled "Ultrasonic Surgical Devices," issued Aug. 17, 1999; U.S. Pat. No. 5,935,144, entitled "Double Sealed Acoustic Isolation Members for Ultrasonic," issued Aug. 10, 1999; U.S. Pat. No. 5,944,737, entitled "Ultrasonic Clamp Coagulator Apparatus Having Improved Waveguide Support Member," issued Aug. 31, 1999; U.S. Pat. No. 5,322,055, entitled "Clamp Coagulator/Cutting System for Ultrasonic Surgical Instruments," issued Jun. 21, 1994; U.S. Pat. No. 5,630,420, entitled "Ultrasonic Instrument for Surgical Applications," issued May 20, 1997; U.S. Pat. No. 5,449,370, entitled "Blunt Tipped Ultrasonic Trocar," issued Sep. 12, 1995; U.S. Pat. No. D594,983, entitled "Handle Assembly for Surgical Instrument," issued Jun. 23, 2009; and/or any other reference cited herein. Still other suitable forms that instrument (10) may take will be apparent to those of ordinary skill in the art in view of the teachings herein.

II. Exemplary Device for Charging Power Source

It will be understood that in some energy based instruments, it may be desirable to use a battery that is operable to provide a relative high discharge rate such as, for example, a lithium polymer battery or a super capacitor. However, it will be appreciated that a higher capacity battery, rather than a higher discharge rate battery, may be desirable as it can simply hold more charge to power the energy based instrument. Examples described herein relate to synergistic combinations of such batteries in a surgical instrument.

Figure 2:
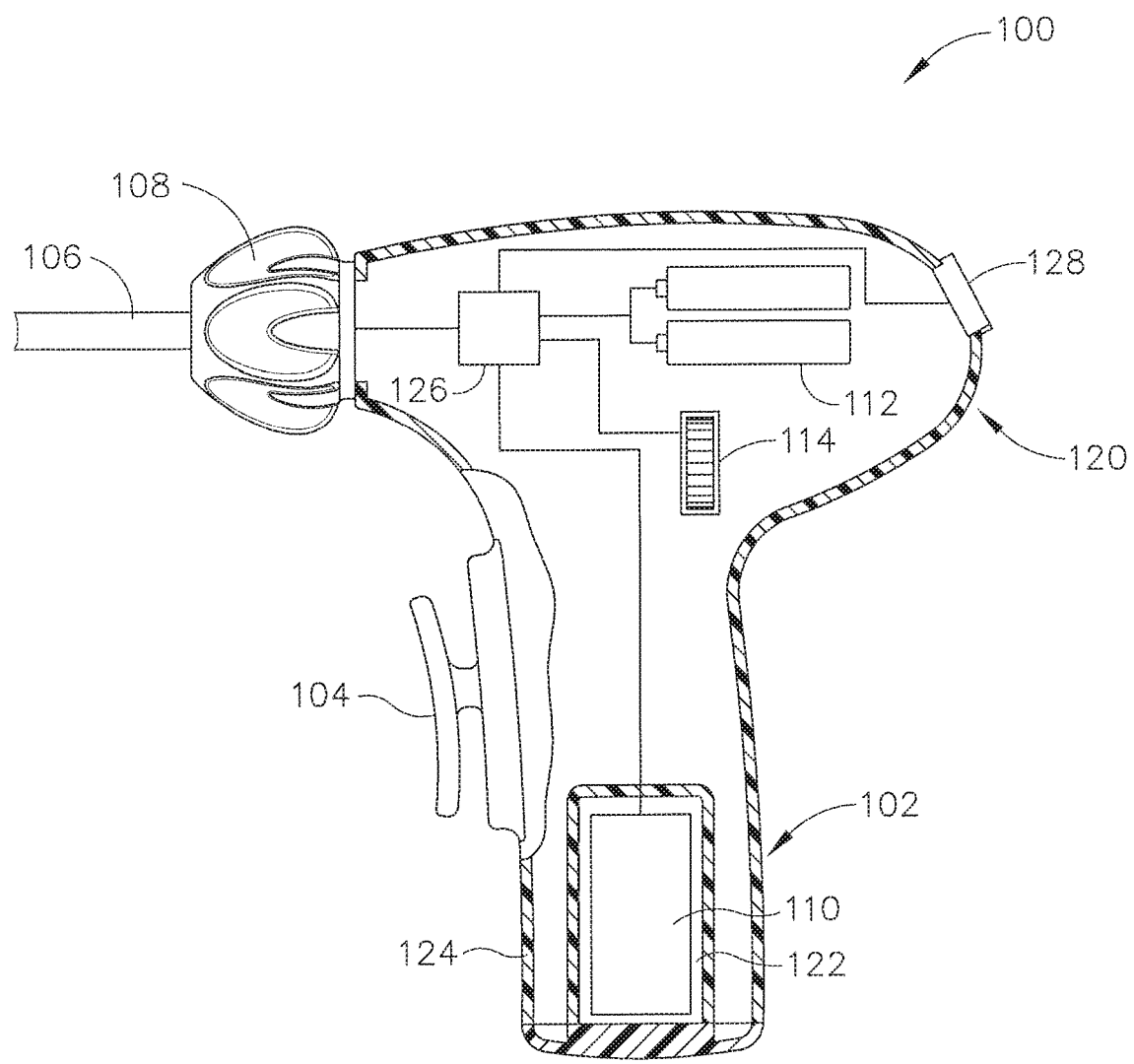
FIG. 2 depicts a partial side cross sectional view of an exemplary alternative version of a surgical instrument.

FIG. 2 shows an exemplary surgical instrument (100) having a grip portion (102) integrated with a body assembly (120). Surgical instrument (100) may be constructed and operable in accordance with at least some of the teachings above and/or teachings of the various references cited herein. A trigger (104) is pivotally coupled with a grip portion (102). A hub (108) is coupled to a distal portion of body assembly (120). A shaft (106) extends distally from hub (108). An end effector, such as end effector (81) of FIG. 1, is positioned at the distal end of shaft (106).

Grip portion (102) is shaped to be held and/or grasped by a single hand of the user. While grasping grip portion (102), the user may also be able to position his/her hand to actuate trigger (104) to use surgical instrument (100). The present example shows grip portion (102) having an elongated, rounded shape, but any suitable shape for grip portion (102) may be used as would be apparent to one of ordinary skill in the art in view of the teachings herein. Grip portion (102) defines an internal battery cavity (122). Battery cavity (122) has a shape and size to hold a power source, such as a storage battery (110), therein. Handle walls (124) surrounding battery cavity (122) are thick enough such that heat given off by storage battery (110) may be absorbed or otherwise insulated from the user's hands by handle walls (124) as storage battery (110) transfers charge to a discharge battery (112), as will be described in further detail below.

Surgical instrument (100) further comprises a switch (114) in communication with grip portion (102). Switch (114) is positioned proximate to grip portion (102) such that the user is able actuate switch (114) with the same hand grasping grip portion (102). Additionally, switch (114) may be positioned such that the user can actuate switch (114) and trigger (104) without repositioning his/her hands. In the present example, switch (114) comprises a sliding switch. However, switch (114) may comprise any suitable component operable to be actuated by the user as would be apparent to one of ordinary skill in the art in view of the teachings herein. For example, switch (114) may comprise a button or toggle lever operable to be actuated by a user.

Switch (114) is in communication with control module (126). Control module (126) is also in communication with discharge battery (112) and storage battery (110). Control module (126) is operable to selectively control the flow of current from storage battery (110) to discharge battery (112) such that storage battery (110) may be used to provide power to discharge battery (112) to increase the available charge of discharge battery (112).

Storage battery (110) of the present example is operable to provide a significant amount of charge for use with surgical instrument (100). However, in order to properly drive the end effector, surgical instrument (100) may have peak power requirements exceeding the capabilities of storage battery (110). Surgical instrument (100) may thus utilize power drawn from discharge battery (112) rather than from storage battery (110) in order to drive the end effector. Discharge battery (112) is operable to deliver a high rate of energy for use by surgical instrument (100). Discharge battery (112) is operable to deliver power directly to end effector (81), or in other exemplary versions, discharge battery may be operable to deliver power to end effector (81) through control module (126).

In the present example, discharge battery (112) may be operable to deliver power to a transducer in communication with end effector (81). Furthermore, while the current example contemplates delivering ultrasonic energy with end effector (81), it will be appreciated that end effector (81) may also be operable to deliver RF energy and/or perform other functions. Discharge battery (112) may comprise, for example, a lithium polymer battery, or any other suitable battery type as would be apparent to one of ordinary skill in the art in view of the teachings herein. In some other exemplary versions, discharge battery (112) comprises a nickel-cadmium battery, a super capacitor, a fuel cell, or any combination thereof. In the event that discharge battery (112) comprises a super capacitor, it will be understood that the super capacitor may initially have a discharged state where thereafter the super capacitor is charged prior to use. Furthermore, discharge battery (112) may comprise a rechargeable battery such that discharge battery (112) may be recharged by storage battery (110) or any other suitable power source such that thereafter discharge battery (112) may again be used to power surgical instrument (100).

Through use of control module (126), switch (114) is operable by the user to cause charge to flow from storage battery (110) to discharge battery (112), thereby sufficiently charging discharge battery (112) for operation of the end effector. Body assembly (120) further comprises at least one visual indicator (128) operable to inform the user of the charge status of discharge battery (112). The present example shows a single visual indicator (128), but any suitable number visual indicators (128) may be used. In some versions, a single visual indicator (128) has different states, such as different colors or brightness levels, to communicate to the user the charge status of discharge battery (112). Visual indicator (128) may comprise an LED, an LCD screen, or any other suitable visual aid as would be apparent to one of ordinary skill in the art in view of the teachings herein.

For example, if discharge battery (112) has a charge level that drops below 50%, visual indicator (128) may signal to the user that discharge battery (112) level is below 50%. The user may then actuate switch (114), which causes control module (126) to direct flow of charge from storage battery (110) to discharge battery (112). As discharge battery (112) charges, control module (126) is operable to determine the charge level of discharge battery (112). Visual indicator (128) may provide real time feedback to the user to indicate the charge status of discharge battery (112). Once charging is complete, visual indicator (128) informs the user that discharge battery (112) is completely charged. In some exemplary versions, control module (126) may be operable to automatically stop delivery of charge from storage battery (110) to discharge battery (112) once discharge battery (112) is fully charged. In other exemplary versions, the user may actuate switch (114) to stop the recharging of discharge battery (112) and monitor the charge level in real time. In some other exemplary versions, storage battery (110) is operable to provide continuous recharge for discharge battery (112) (e.g., such that switch (114) is omitted). Other suitable charging patterns may be used as would be apparent to one of ordinary skill in the art in view of the teachings herein.

Body assembly (120) and grip assembly (102) fully enclose storage battery (110) and discharge battery (112) in the present example. Thus, once surgical instrument (100) is shipped in a package, it will be further understood that surgical instrument (100) is ready for use since storage battery (110) and discharge battery (112) are already contained within surgical instrument (100). Storage battery (110) may already be fully charged, and in some instances discharge battery (112) may also be fully charged before instrument (100) is removed from the package. Once removed from a package or other suitable container, surgical instrument (100) may be used within approximately five minutes or any other suitable time period. In addition or in the alternative, surgical instrument (100) may be removed from a package and stored for a period of time prior to use. Prior to use of surgical instrument (100), it will be appreciated that since discharge battery (112) and storage battery (110) are contained within surgical instrument (100), surgical instrument (100) may be sterilized using an ethylene oxide sterilization method and/or any other suitable sterilization method as would be apparent to one of ordinary skill in the art in view of the teachings herein.

Figure 3:
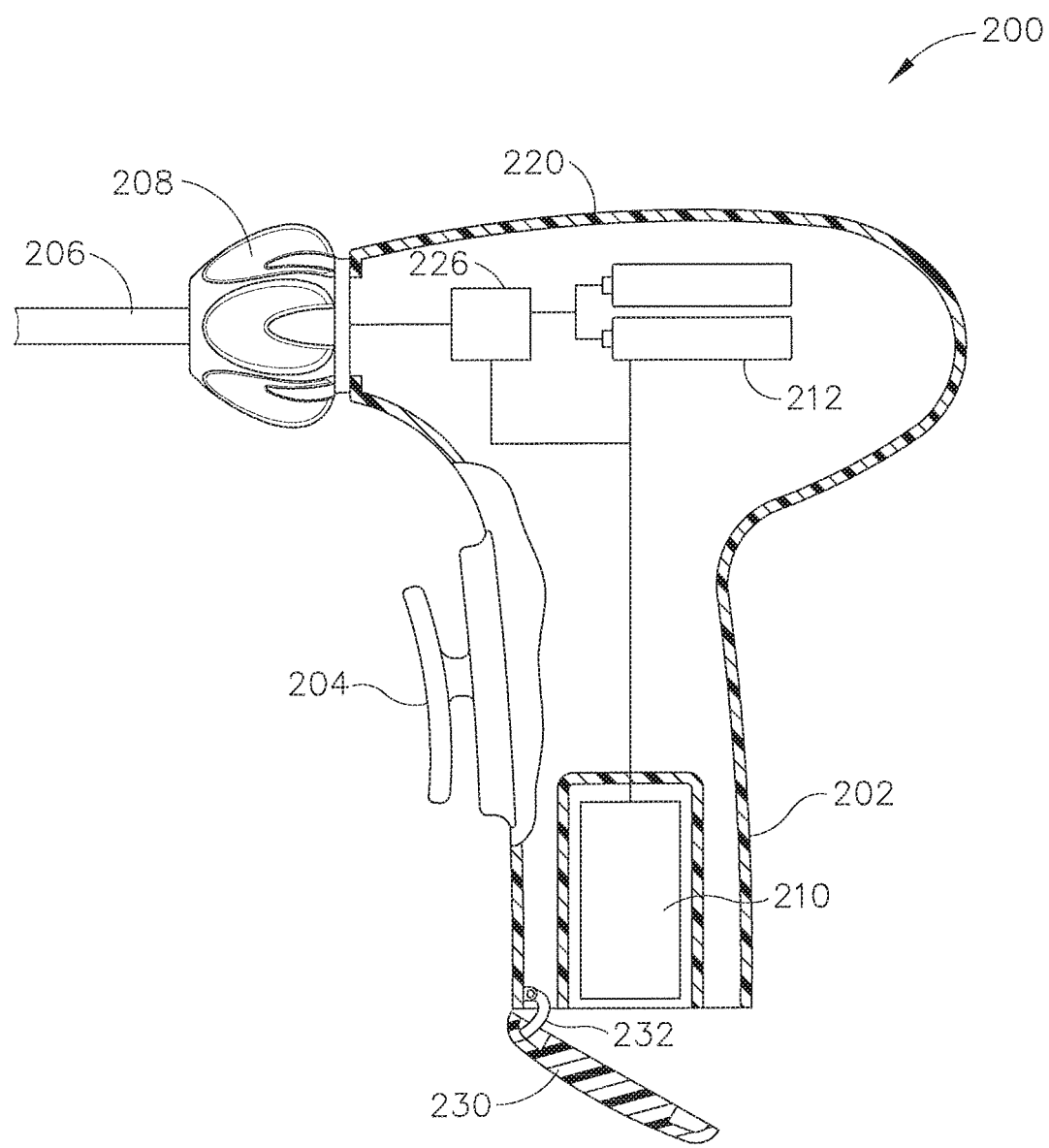
FIG. 3 depicts a partial side cross sectional view of another exemplary alternative version of a surgical instrument having a battery door.

FIG. 3 shows an exemplary surgical instrument (200) having grip portion (202) integrated with body assembly (220). Grip portion (202) includes a pivoting trigger (204). A hub (208) is connected to a distal portion of body assembly (220). A shaft (206) extends distally from hub (208). An end effector (not shown) is positioned at the distal end of shaft (206). Surgical instrument (200) of this example is substantially similar to surgical instrument (100) of FIG. 1, with the exception that grip portion (202) comprises a battery door (230) pivotally coupled with surgical instrument (200) by a hinge (232). While the present example shows hinge (232) connecting battery door (230) to grip portion (202), it will be appreciated that any suitable connection feature may be used as would be apparent to one of ordinary skill in the art in view of the teachings herein. For example, a screw-on or snap-fit cap may be used instead of battery door (230). When battery door (230) is closed, battery door (230) is operable to form a hermetic seal or any other suitable level of sealing with grip portion (202). Thus, it will be understood that storage battery (210) used with surgical instrument (200) for charging discharge battery (212) may be replaced when storage battery (210) has been depleted. In some other versions, it will be appreciated that storage battery (210) may be shipped disconnected from surgical instrument (200) where the user may then insert storage battery (210) into grip portion (202) when surgical instrument (200) is ready for use.

Surgical instrument (200) also comprises control module (226). In the present example, control module (226) is operable to coordinate delivery of power and charging as depicted by chart (350) of FIG. 4. In some exemplary versions, control module (226) may be integrally formed with surgical instrument (200) or in the alternative, control module (226) may be detachable. Storage battery (210) may be operable to deliver power to power surgical instrument (200) directly rather than through discharge battery (212). In such a configuration, discharge battery (212) may comprise a super capacitor operable to supplement the power delivery of storage battery (210). It will be understood that the power drawn from surgical instrument (200) may not necessarily be constant. As a result, storage battery (210) is operable to satisfy most of the power needs of surgical instrument (200). In the event that the power requirements of surgical instrument (200) fall below a level of what storage battery (210) is able to provide, control module (226) directs the excess charge to charge the super capacitor. In the event that the power needs of surgical instrument (200) exceed a level of power that storage battery (210) can deliver, then the super capacitor may be directed by control module (226) to supplement the additional needed power. In the event that storage battery (210) provides the appropriate amount of power for surgical instrument (200), then it will be appreciated that the super capacitor will neither be charging nor discharging. An example of the relative power amounts of storage battery (210), power required by surgical instrument (200), and power in a super capacitor are shown in FIG. 4 using a storage battery line (300), a power requirement line (302), and a capacitor line (304), respectively, where the horizontal axis represents time, which may be indicated using any suitable unit of time and the vertical axis represents charge state, which may be indicated using any suitable unit of charge.

Figure 4:
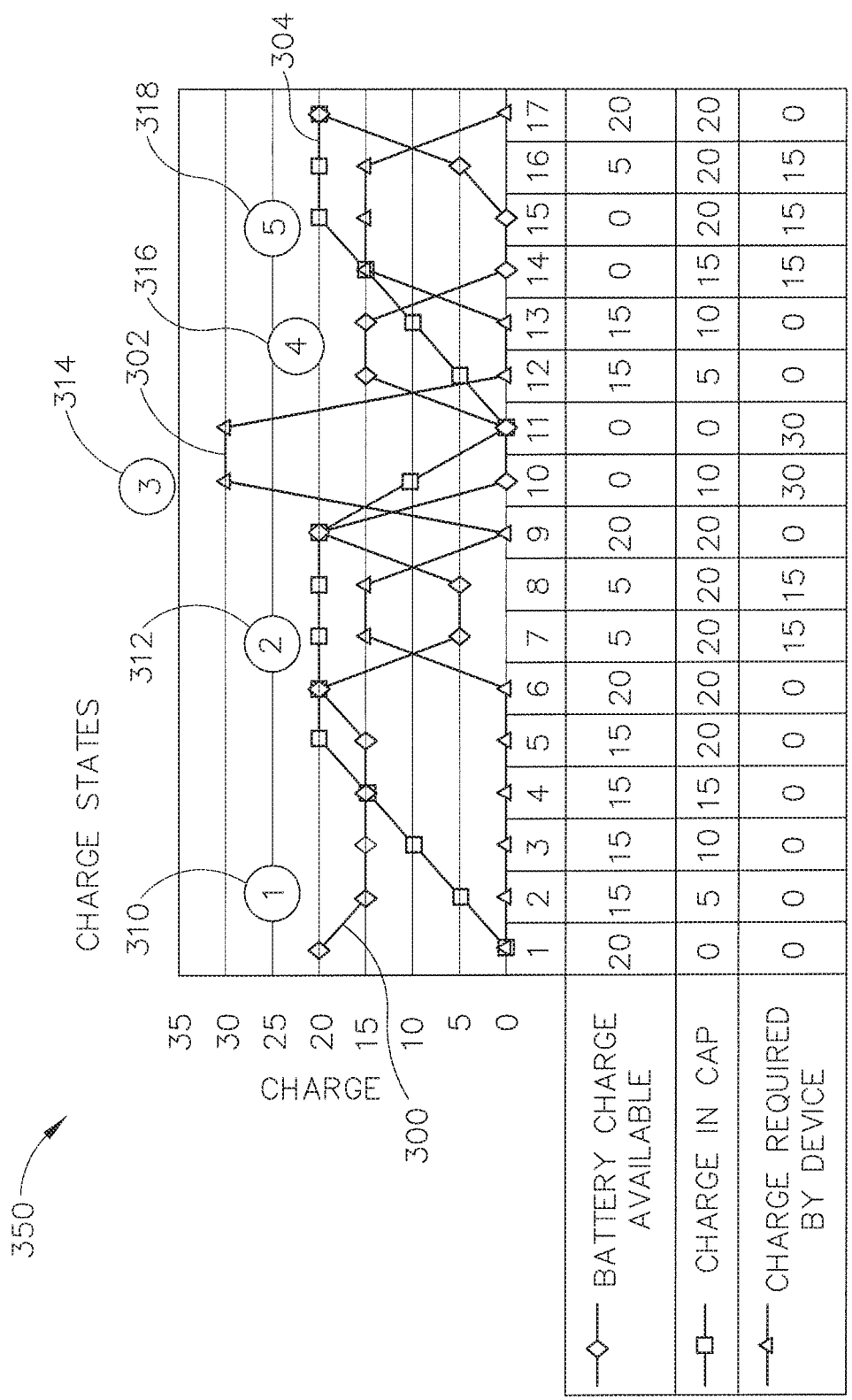
FIG. 4 depicts a diagrammatic view of a graph showing coordinated power delivery used by the surgical instrument of FIG. 3.

In FIG. 4, which demonstrates a merely exemplary charge state sequence, stage 1 (310) shows a state where surgical instrument (200) does not require any power. As a result, storage battery (210) may continuously charge discharge battery (212). At stage 2 (312), surgical instrument (200) requires some amount of power (e.g., when surgical instrument (200) is powered on, etc.). Storage battery (210) switches to supply power to surgical instrument (200) and discharge battery (212) remains charged. Since at stage 2 (312), storage battery (210) is being used to provide power to surgical instrument (200), charging of discharge battery (212) has halted. It should be understood, however, that storage battery (210) may simultaneously provide power to surgical instrument (200) and charge discharge battery (212) in some instances. At stage 3 (314), the power requirement of surgical instrument (200) spikes (e.g., in response to actuation of trigger (204), etc.) and both discharge battery (212) and storage battery (210) must be used to supply sufficient power to surgical instrument (200). Thereafter at stage 4 (316), the power required by surgical instrument (200) drops significantly and therefore, discharge battery (212) may be recharged again using storage battery (210). Finally, at stage 5 (318), the power needs of surgical instrument (200) rise again and storage battery (210) is used to provide power to surgical instrument (200) and discharge battery (212) is no longer charged by storage battery (210). While FIG. 4 shows merely one exemplary charging sequence relationship between discharge battery (212), storage battery (210) and surgical instrument (200), it will be appreciated that other sequences may be used as would be apparent to one of ordinary skill in the art in view of the teachings herein. It will be appreciated that the above-described sequence for charging discharge battery (212) and/or storage battery (210) may be controlled wholly or in part by control module (126, 226) described above. In some alternative versions, it will be appreciated that a separate module (not shown) may be used to control the charging of discharge battery (212) and storage battery (210).

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments of the present invention have application in conventional endoscopic and open surgical instrumentation as well as application in robotic-assisted surgery. For instance, those of ordinary skill in the art will recognize that various teaching herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A method of powering an end effector of a surgical instrument, the surgical instrument comprising the end effector, a control circuit in communication with the end effector, a first power source in communication with the control circuit, and a second power source in communication with the control circuit, wherein the first and second power sources are different types of power sources, the method comprising:
   (a) powering the end effector with the first power source, independently of the second power source, via the control circuit to meet a first required load, wherein the first power source charges the second power source while powering the end effector at the first required load;
   (b) detecting an increase in the first required load to a second required load to power the end effector via the control circuit, wherein the first power source is incapable of powering the end effector to meet the second required load; and
   (c) in response to detecting the increase in the first required load to the second required load, supplementing the first power source with the second power source via the control circuit to meet the second required load by powering the end effector via the control circuit using the first and second power sources simultaneously.

2. The method of claim 1, wherein the first power source comprises a storage battery.

3. The method of claim 1, wherein the second power source comprises a supercapacitor.

4. The method of claim 1, wherein the control circuit automatically supplements the first power source with the second power source to meet the second required load to power the end effector.

5. The method of claim 1, wherein the first power source stops charging the second power source while powering the end effector at the second required load.

6. The method of claim 1, wherein the first power source stops charging the second power source when the second power source reaches a maximum capacity.

7. The method of claim 1, wherein the second power source supplements the first power source at a first rate of discharge, wherein the first power source powers the end effector at a second rate of discharge, wherein the first rate of discharge is greater than the second rate of discharge.

8. The method of claim 1, wherein the surgical instrument further comprises a switch in communication with the control circuit, wherein the control circuit stops charging the second power source with the first power source based on a position of the switch.

9. The method of claim 1, wherein the control circuit ceases the second power source from providing power to the end effector while still providing power to the end effector with the first power source.

10. A method of powering an end effector of a surgical instrument, the surgical instrument comprising the end effector, a control circuit in communication with the end effector, a first power source in communication with the control circuit, and a second power source in communication with the control circuit, wherein the first and second power sources are different types of power sources, the method comprising:
   (a) activating the end effector with the first power source, independently of the second power source, via the control circuit at a first power load;
   (b) detecting, via the control circuit, that the second power source is charged to a power level below a charge threshold; and
   (c) charging the second power source, via the control circuit, to at least the charge threshold with the first power source while the first power source continues to activate the end effector at the first power load, wherein the second power source is capable of activating the end effector independently of the first power source when the second power source is charged at the charge threshold.

11. The method of claim 10, further comprising activating the end effector at a second power load that is greater than the first power load.

12. The method of claim 11, further comprising activating the end effector at the second power load with the second power source, independently of the first power source.

13. The method of claim 12, wherein second power source activates the end effector at the second power load with the charge provided to the second power source by the first power source.

14. The method of claim 13, wherein the first power source is incapable of activating the end effector at the second power load independently of the second power source.

15. A method of powering an end effector of a surgical instrument, the surgical instrument comprising the end effector, a control circuit in communication with the end effector, a first power source in communication with the control circuit, and a second power source in communication with the control circuit, wherein the first and second power sources are different types of power sources, the method comprising:
(a) determining, via the control circuit, whether the end effector requires power in a high demand scenario, a medium demand scenario, or a low demand scenario, wherein the high demand scenario requires a greater power load than the medium demand scenario, wherein the medium demand scenario requires a greater power load than the low demand scenario;
(b) if the control circuit determines that the end effector requires power in the high demand scenario, then the control circuit provides that the first power source and the second power source together simultaneously activate the end effector;
(c) if the control circuit determines that the end effector requires power in the medium demand scenario, then the control circuit provides that the first power source activates the end effector independently of the second power source without charging the second power source; and
(d) if the control circuit determines that the end effector requires power in the low demand scenario, then the control circuit provides that the first power source activates the end effector independently of the second power source and simultaneously charges the second power source.

16. The method of claim 15, wherein the control circuit provides that the end effector is powered in the low demand scenario prior to the end effector being powered in either the high demand scenario or the medium demand scenario.

17. The method of claim 16, wherein the first power source charges the second power source to a maximum charge in the low demand scenario.

18. The method of claim 15, wherein the second power source is fully charged while the first power source activates the end effector in the medium demand scenario.

19. The method of claim 15, wherein the second power source is not fully charged while the first power source activates the end effector in the medium demand scenario.

20. The method of claim 15, wherein the control circuit provides that the end effector is powered in the medium demand scenario prior to the end effector being powered in the high demand scenario.

* * * * *